(12) United States Patent
McDonald

(10) Patent No.: US 9,517,110 B2
(45) Date of Patent: Dec. 13, 2016

(54) MATRIX BAND RETAINER

(71) Applicant: DENTSPLY INTERNATIONAL INC., York, PA (US)

(72) Inventor: Simon P. McDonald, Katikati (NZ)

( * ) Notice: Subject to any disclaimer, the term of this patent is extended or adjusted under 35 U.S.C. 154(b) by 291 days.

(21) Appl. No.: 14/355,937

(22) PCT Filed: Nov. 2, 2012

(86) PCT No.: PCT/US2012/063455
§ 371 (c)(1),
(2) Date: May 2, 2014

(87) PCT Pub. No.: WO2013/067455
PCT Pub. Date: May 10, 2013

(65) Prior Publication Data
US 2014/0302456 A1  Oct. 9, 2014

(30) Foreign Application Priority Data
Nov. 2, 2011 (NZ) ........................................ 596176

(51) Int. Cl.
*A61C 5/12* (2006.01)

(52) U.S. Cl.
CPC *A61C 5/12* (2013.01); *A61C 5/125* (2013.01)

(58) Field of Classification Search
CPC .................................. A61C 5/125; A61C 5/12
See application file for complete search history.

(56) References Cited

U.S. PATENT DOCUMENTS

| | | | | |
|---|---|---|---|---|
| 2,502,903 A | * | 4/1950 | Toffiemire | A61C 5/125 433/155 |
| 2,588,059 A | | 3/1952 | Tofflemire | |
| 2,686,970 A | * | 8/1954 | Reiter | A61C 5/125 433/155 |
| 2,687,573 A | * | 8/1954 | Stone | A61C 5/125 433/155 |
| 2,709,302 A | * | 5/1955 | Reiter | A61C 5/125 433/155 |

(Continued)

OTHER PUBLICATIONS

International Search Report, PCT/US2012/063455, International Searching Authority: European Patent Office, Authorized Officer: Roche, Oliver, Mailing Date: Mar. 1, 2013.

*Primary Examiner* — Cris L Rodriguez
*Assistant Examiner* — Hao D Mai
(74) *Attorney, Agent, or Firm* — Leana Levin; Doug Hura; David Zdurne

(57) ABSTRACT

A denial matrix band retainer is provided with a retractor, main body portion and a bias mechanism. The retractor includes a proximal end and a distal end, with a band engagement portion at the proximal end. The main body portion having a proximal end and a distal end, with a head portion located at the proximal end. The bias mechanism coupling the retractor to the main body portion, the bias mechanism having a static position and a fully active position, wherein in the static position the head portion is spaced apart from the band engagement portion a first distance, and in the fully active position the head portion is spaced apart from the band engagement portion a second distance which is greater than the first distance, the bias mechanism including an actuator for urging the bias mechanism towards the fully active position.

9 Claims, 11 Drawing Sheets

(56) References Cited

U.S. PATENT DOCUMENTS

| | | | | |
|---|---|---|---|---|
| 2,722,746 | A * | 11/1955 | Brenner | A61C 5/125 433/161 |
| 2,786,273 | A * | 3/1957 | Reiter | A61C 5/125 433/155 |
| 2,853,782 | A * | 9/1958 | Gruenwald | A61C 5/125 433/155 |
| 2,964,847 | A * | 12/1960 | Tofflemire | A61C 5/125 433/155 |
| 3,085,339 | A * | 4/1963 | Wolfe | A61C 7/04 433/4 |
| 3,145,473 | A * | 8/1964 | Tofflemire | A61C 5/125 433/155 |
| 3,152,400 | A | 10/1964 | Lang | |
| 3,237,307 | A | 3/1966 | Tofflemire | |
| 3,377,705 | A * | 4/1968 | Tofflemire | A61C 5/125 29/453 |
| 3,436,831 | A * | 4/1969 | Tofflemire | A61C 3/14 433/155 |
| 3,516,162 | A * | 6/1970 | Ainsworth | A61C 5/125 433/155 |
| 3,613,245 | A * | 10/1971 | Knight | A61C 5/125 433/155 |
| 3,699,595 | A * | 10/1972 | Tofflemire | A61C 5/125 433/159 |
| 3,908,273 | A * | 9/1975 | Reiter | A61C 5/125 433/155 |
| 4,310,305 | A * | 1/1982 | Frajdenrajch | A61C 7/04 433/155 |
| 4,334,864 | A * | 6/1982 | Rubino | A61C 3/14 433/156 |
| 4,436,510 | A * | 3/1984 | Klein | A61C 7/306 206/390 |
| 4,915,627 | A * | 4/1990 | Hirdes | A61C 5/125 433/155 |
| 5,055,045 | A * | 10/1991 | Dickie | A61C 5/125 433/155 |
| 5,342,197 | A * | 8/1994 | Stein | A61C 5/125 433/155 |
| 5,460,525 | A * | 10/1995 | Rashid | A61C 5/125 433/155 |
| 5,584,692 | A * | 12/1996 | Weissenfluh | A61C 5/125 433/155 |
| 5,722,831 | A * | 3/1998 | Lin | A61C 5/125 433/155 |
| 6,234,793 | B1 | 5/2001 | Brattesani | |
| 6,293,796 | B1 * | 9/2001 | Trom | A61C 5/125 433/139 |
| 6,345,983 | B1 * | 2/2002 | Godfrey | A61C 5/125 433/159 |
| 7,165,970 | B2 * | 1/2007 | Anderson | A61C 5/122 433/138 |
| 8,052,420 | B2 * | 11/2011 | Navarro | A61C 7/04 433/155 |
| 2011/0053111 | A1 * | 3/2011 | Zand | A61C 7/00 433/148 |

* cited by examiner

MATRIX BAND RETAINER

CROSS-REFERENCE TO RELATED APPLICATION

This application claims the priority to New Zealand Application No. 596176, filed Nov. 2, 2011, the entire contents of which is hereby incorporated by reference.

FIELD OF THE INVENTION

The present invention relates to a retainer for use with a dental matrix band, and in particular, a dental matrix band retainer for securing a circumferential matrix band during tooth restorations.

BACKGROUND OF THE INVENTION

Circumferential matrix bands and the use of matrix bands are well known and widely utilized in restorative dentistry.

The main problem with the prior art is that circumferential bands either require tensioners to be left in place during the restoration procedure to retain the tension on the matrix band, or the band is tensioned into a barrel-type feature. In both cases the restoration procedure is restricted by the presence of the tensioning device.

A dental matrix retainer is a mechanical device that clamps the matrix band and fixes it around the tooth during tooth restoration. It usually consists of a main body element and a head element. The matrix band is fitted through the head element and the main body provides for the tightening of the matrix band around the tooth. As suggested above, the problem with the prior art is that matrix band retainers are left attached to the circumferential band during the restoration and are a source of interference to the dentists.

Prior art matrix band retainers can be made out of different materials such as plastics and metal. They may be disposable or non-disposable.

SUMMARY OF THE INVENTION

It is an object of the present invention to provide a means for placing and tightening a circumferential matrix band around a tooth.

It is an object of the present invention to provide a easy to use circumferential dental matrix band retainer.

It is a further object of the present invention to include a circumferential matrix band which once placed, offers less obstruction in the restoration area.

It is yet a further object of the present invention to provide a matrix band retainer that can be detached from the toggled circumferential band once the band is tightened around the tooth. The present invention therefore provides a dental matrix band retainer. The retainer includes a retractor having a proximal end and a distal end, with a band engagement portion at the proximal end, a main body portion having a proximal end and a distal end, with a head portion located at the proximal end, and a bias mechanism coupling the retractor to the main body portion, the bias mechanism having a static position and a fully active position, wherein in the static position the head portion is spaced apart from the band engagement portion a first distance, and in the fully active position the head portion is spaced apart from the band engagement portion a second distance which is greater than the first distance, the bias mechanism including an actuator for urging the bias mechanism from the static position towards the fully active position.

DETAILED DESCRIPTION OF THE INVENTION

Figure 1:
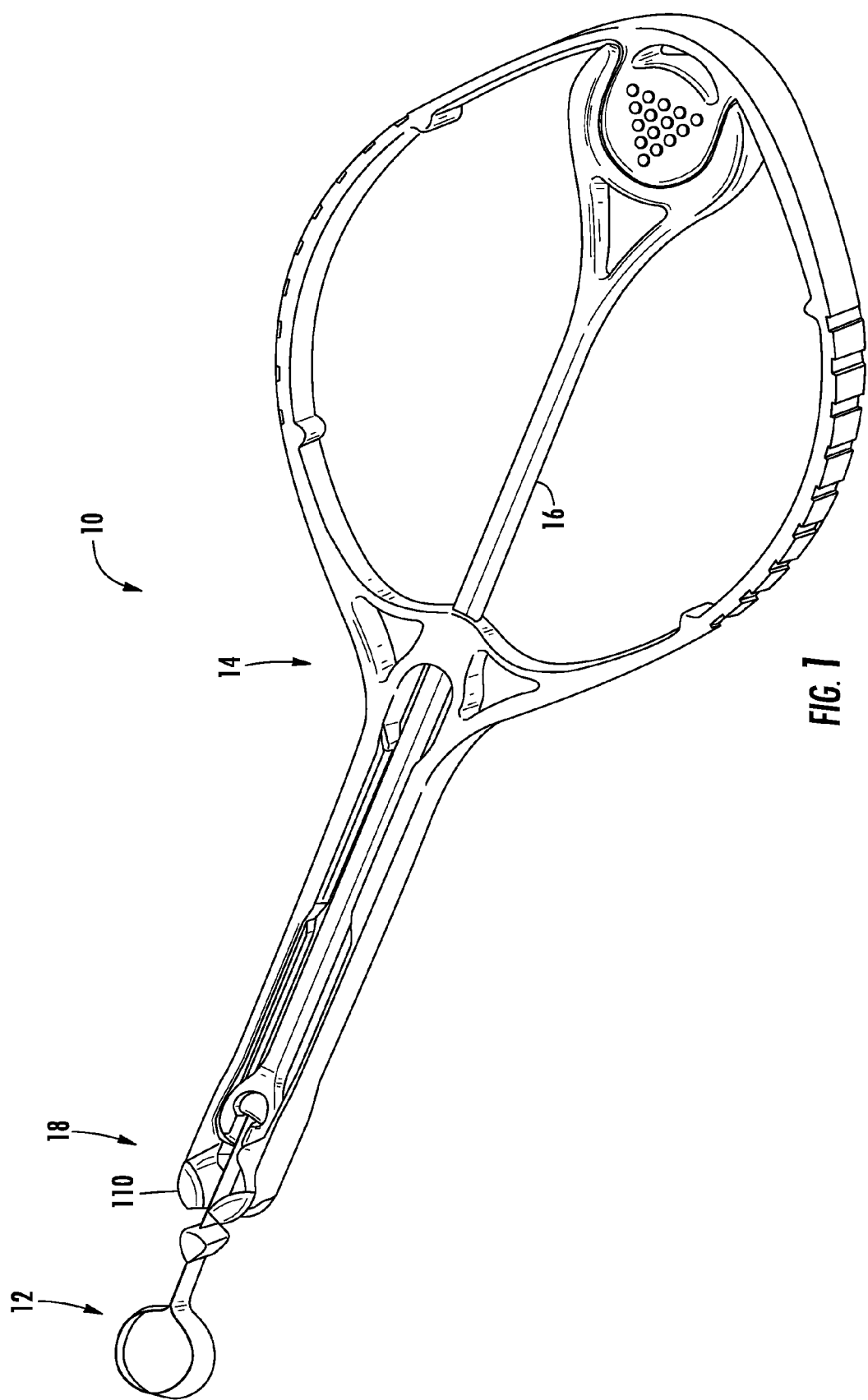
FIG. 1 is a perspective view of a circumferential dental matrix band retainer in accordance with one embodiment of the present invention, together with a circumferential dental matrix.

FIG. 1 is a perspective view of a circumferential dental matrix band retainer 10 in accordance with one embodiment of the present invention, together with a circumferential dental matrix 12. The retainer 10 is shown to include a main body portion 14 and a retractor 16. The main body portion 14 includes a head portion 18.

Figure 2:
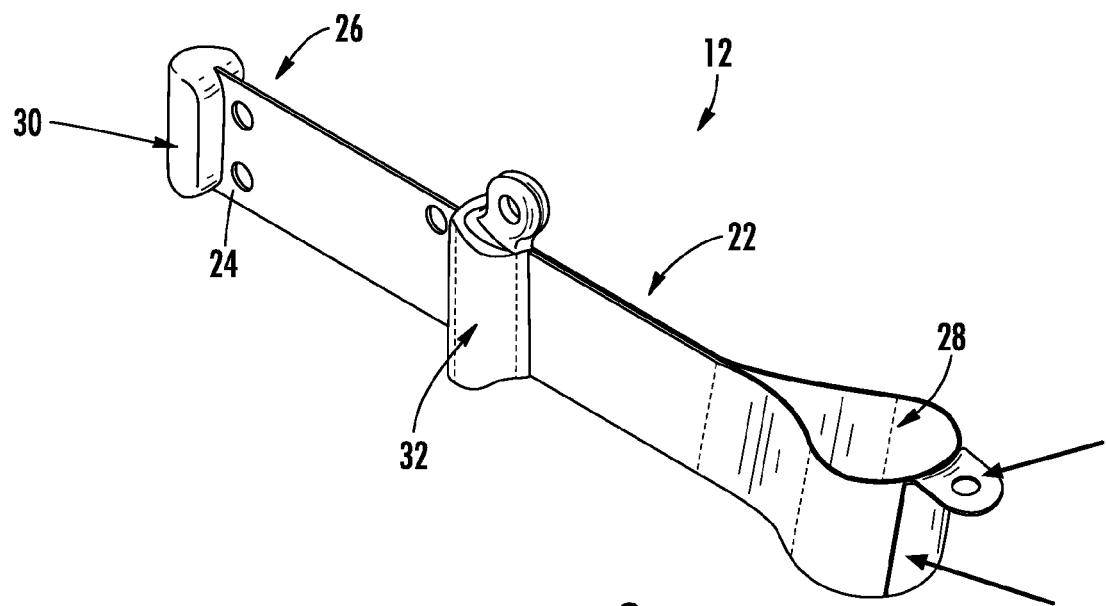
FIG. 2 is a perspective view of the circumferential dental matrix band of FIG. 1.

The circumferential dental matrix 12 is shown in FIG. 2. Although the invention does not relate to the circumferential dental matrix 12, the structure is important for a better understanding of the invention. The circumferential dental matrix 12 includes a band 32 having a first end 24 and a second end 26. The band is folded back over with the ends aligned so as to form a circumferential band portion 28. The ends are secured together via a fixed toggle 30 or the like. A movable or sliding toggle 32 is formed over the band, with an interference fit. As will be appreciated, as the movable toggle is advanced away from the ends, the movable toggle will restrict the size of the circumference of the looped band.

Figure 6:
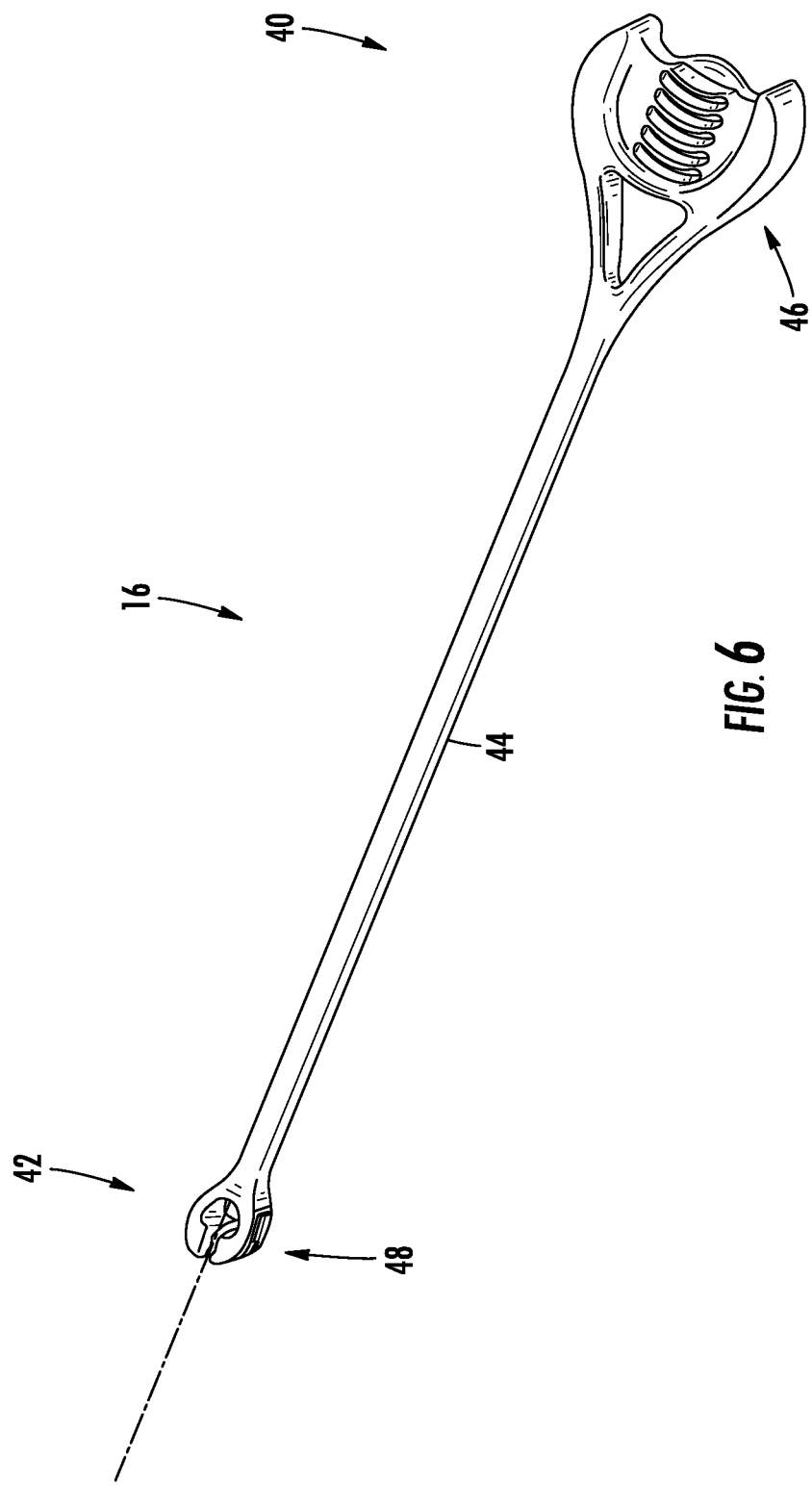
FIG. 6 is a perspective view of the retractor of the circumferential dental matrix band retainer of FIG. 1.
Figure 7:
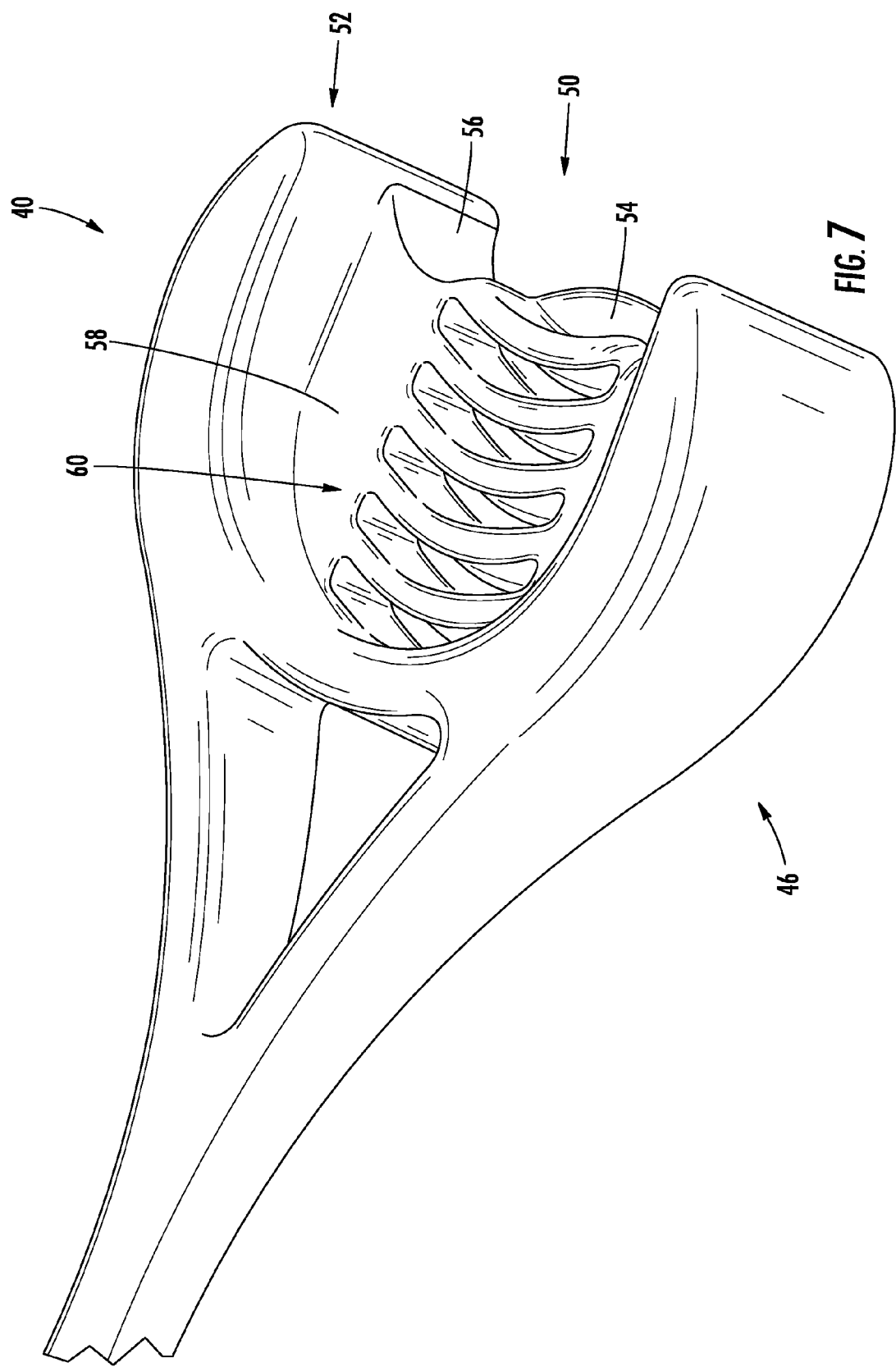
FIG. 7 is a perspective view of the distal end of the retractor of the circumferential dental matrix band retainer of FIG. 1.
Figure 8:
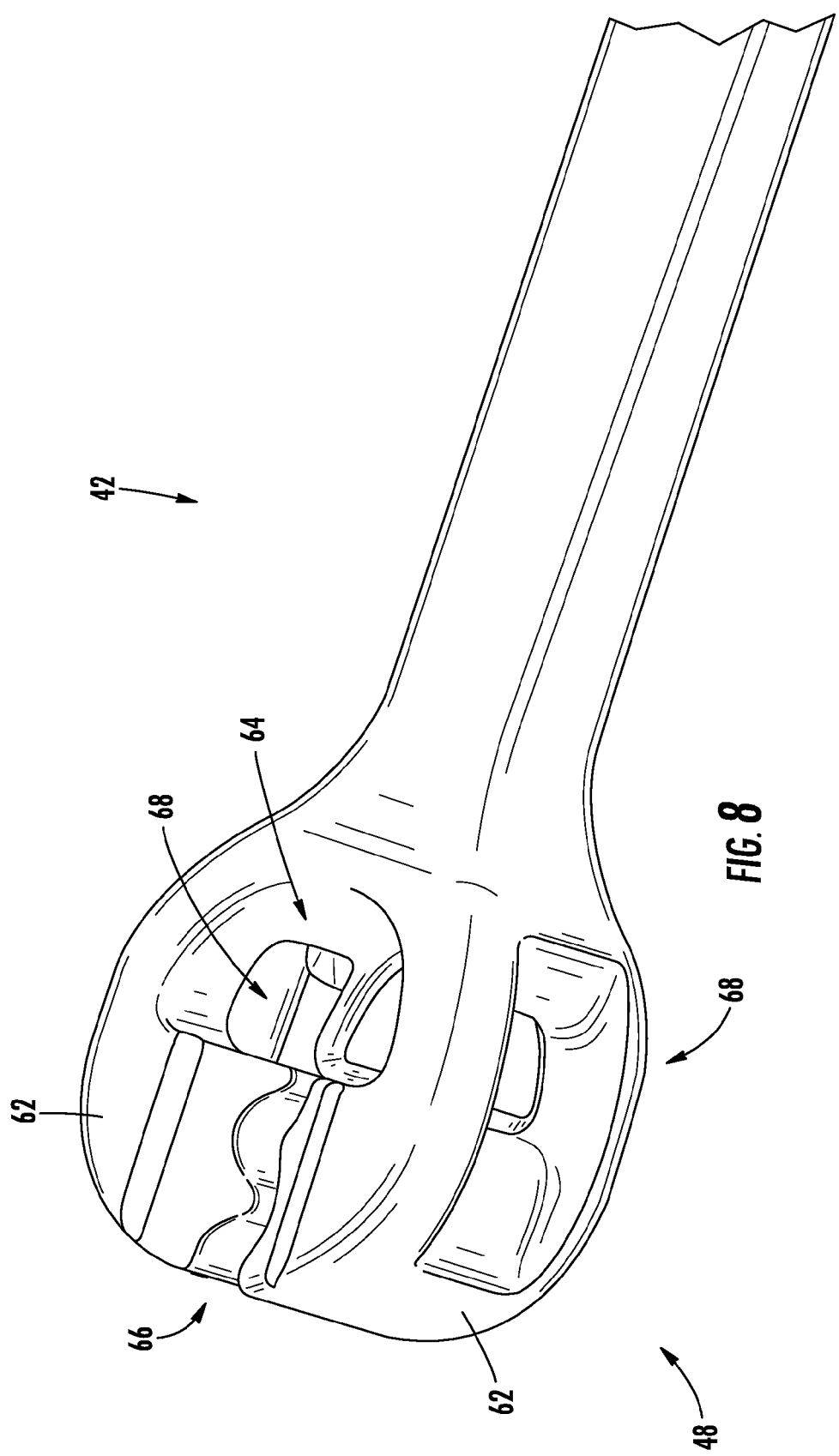
FIG. 8 is a perspective view of the proximal end of the retractor of the circumferential dental matrix band retainer of FIG. 1.

FIG. 6 is a perspective top view of the retractor 16. FIG. 7 is a perspective view of the distal end 40 of the retractor and FIG. 8 is a perspective view of the proximal end 42 of the retractor. FIGS. 6-8 show that the retractor 16 includes a rod portion 44 with a connector 46 at the distal end and a coupler 48 at the proximal end. The retractor 16 may be made of various materials which will present a rigid structure, including plastic and metal, for example. The connector, as best seen in FIG. 7, includes a coupler like structure having an open distal end 50. The connector as shown includes an open top side 52 and a wall 54 providing a close bottom side 56. An inner surface 58 of the wall includes a series of similar shaped curved grooves 60. As best seen in FIG. 8, the coupler includes a generally C-shaped profile formed in part by a pair of prongs 62. The prongs form a generally D-shaped opening 64 from which extends a slot 66 towards and opening at the proximal end of the retractor. The slot presents a serpentine shape for added gripping action as will be understood. The sides of the coupler each include a groove 68 extending in a longitudinal direction.

Figure 3:
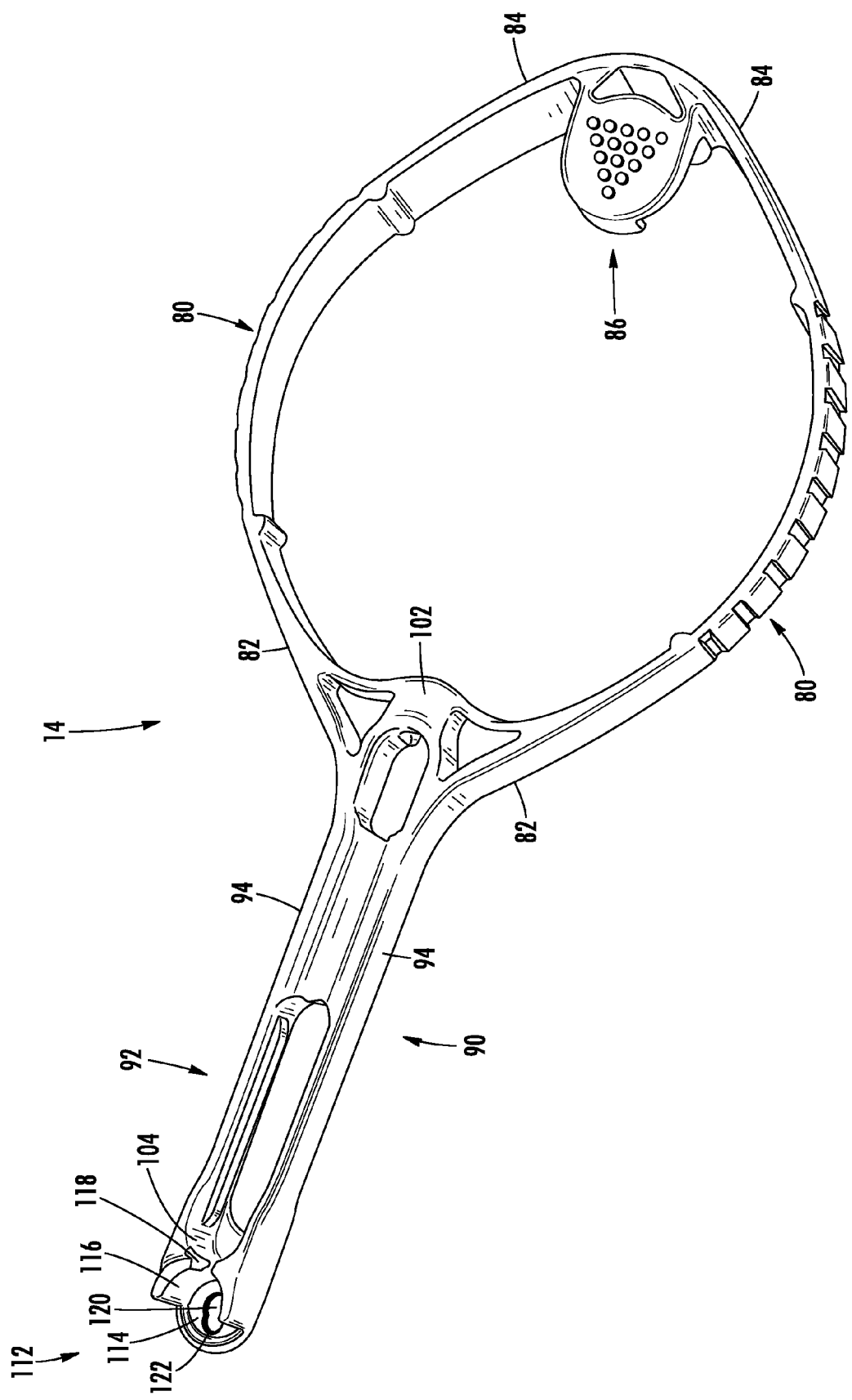
FIG. 3 is a perspective top view of the main body portion of the circumferential dental matrix band retainer of FIG. 1.

FIG. 3 is a perspective top view of the main body portion 14 of the circumferential dental matrix band retainer 10. The main body portion 14 includes a pair of flexible outer arms 80 in the shape of a bow. The arms each include a first end 82 and a second end 84. The first ends meet at a generally mid-portion of the main body portion 14. The second ends meet at a distal location of the main body portion 14. A connector 86 for connecting to the retractor is located at the distal end of the main body portion.

A neck portion 90 extends from the first ends of the flexible outer arms to a proximal end of the main body portion 14. The neck portion includes a channel 92 for receiving and retaining the retractor 16. The channel is formed by a pair of opposed facing sidewalls 94. The channel includes opposing tongue portions 96 extending in a longitudinal direction along an inner surface of the sidewalls. The tongues are adapted to be received by the pair of grooves in the coupler to provide added rigidity. The lower portion of the side walls are connected via a first bottom wall 98 located adjacent the first ends of the pair of flexible outer arms. The lower portions of the sidewalls are further connected via a second bottom wall 100 located at the proximal end of the main body portion. The upper portions of the sidewalls are connected by a top wall or bridge 102 located generally where the first ends of the flexible outer arms converge. The neck portion further includes a retractor abutment 104 which limits travel of the retractor in a proximal direction.

Figure 4:
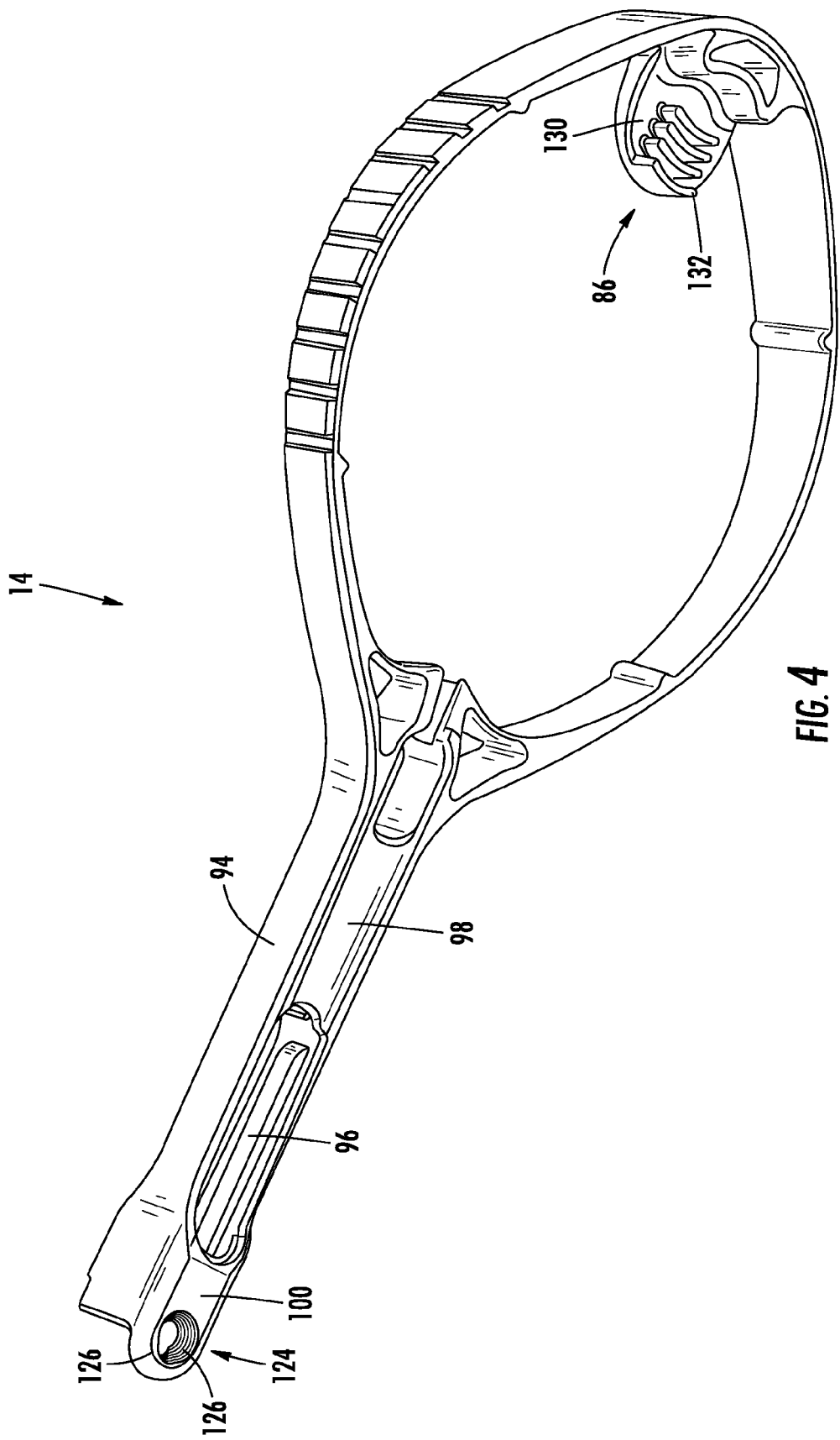
FIG. 4 is a perspective bottom view of the main body portion of the circumferential dental matrix band retainer of FIG. 1.
Figure 5:
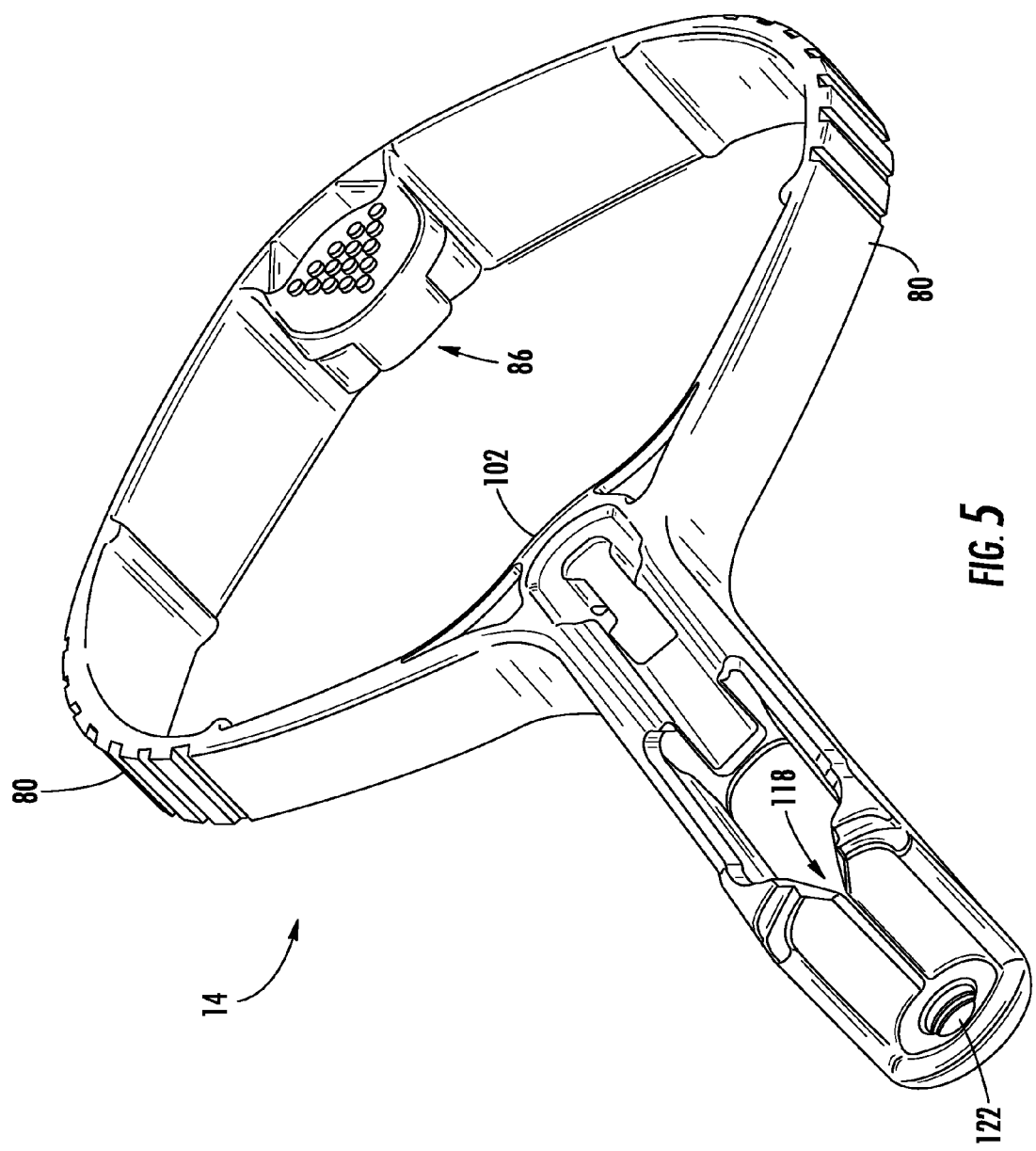
FIG. 5 is a perspective front top view of the main body portion of the circumferential dental matrix band retainer of FIG. 1.

As shown in FIG. 1, the main body portion 14 includes the head portion. The head portion includes a generally cylindrical shaped swivel head 110. As seen in FIG. 3, the head portion includes a receptacle 112 for receiving the swivel head. The receptacle includes a portion of the second bottom wall. An upper surface of the second bottom wall provides a generally cylindrical recess 114. Extending upward from a distal perimeter of the upper surface is a swivel head abutment or wall 116 presenting a cylindrical surface generally aligned with the generally cylindrical recess, as well as the swivel head. The swivel head wall is divided by a vertically extending slot 118. The slot is generally aligned with a longitudinal axis extending through the neck portion. It will be appreciated that the swivel head wall and the retractor abutment are formed by the same structure in this embodiment. A circular opening 120 extends through the second bottom wall generally centered with the cylindrical recess. A slotted opening 122 extends from the circular opening towards the proximal end of the main body portion. The circular opening and slotted opening together generally form the shape of a key hole. As seen in FIG. 4, the key hole opening includes an undercut 124 extending along the circumference of the keyhole opening and having a radius generally the same as the slotted opening, but slightly larger beginning with a most distal location along the circumference and extending in both direction for a total circumference of approximately 225 degrees. Thus, a first and second stop 126 are formed.

Figure 11:
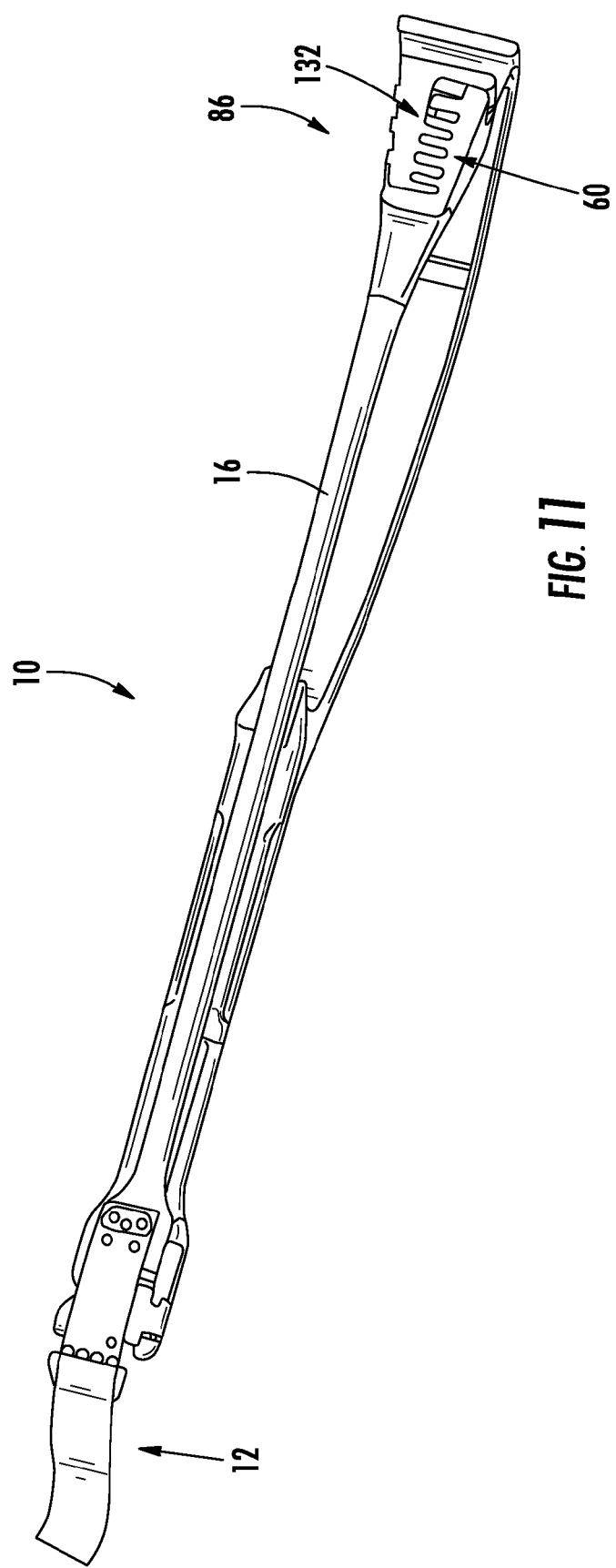
FIG. 11 is a cross-sectional view of the circumferential dental matrix band retainer of FIG. 1.

FIG. 4 also shows the connector. The connector includes a wall 130 extending from the distal end of the main body portion towards the proximal end and from the top side of the main body portion. From an inner surface of the connector wall, a series of similar shaped curved flanges 132 extend vertically toward the bottom side of the main body portion. The curved flanges or prongs are adapted to mate with the curved grooves of the retractor, such as shown in FIG. 11. It will be appreciated that the position of the retractor along a longitudinal axis of the main body portion may be adjusted by changes the position of the curved flanges being inserted in respective curved grooves. The vertical prongs provide an adjustable reach on the head portion to allow for material stretch.

Figure 9:
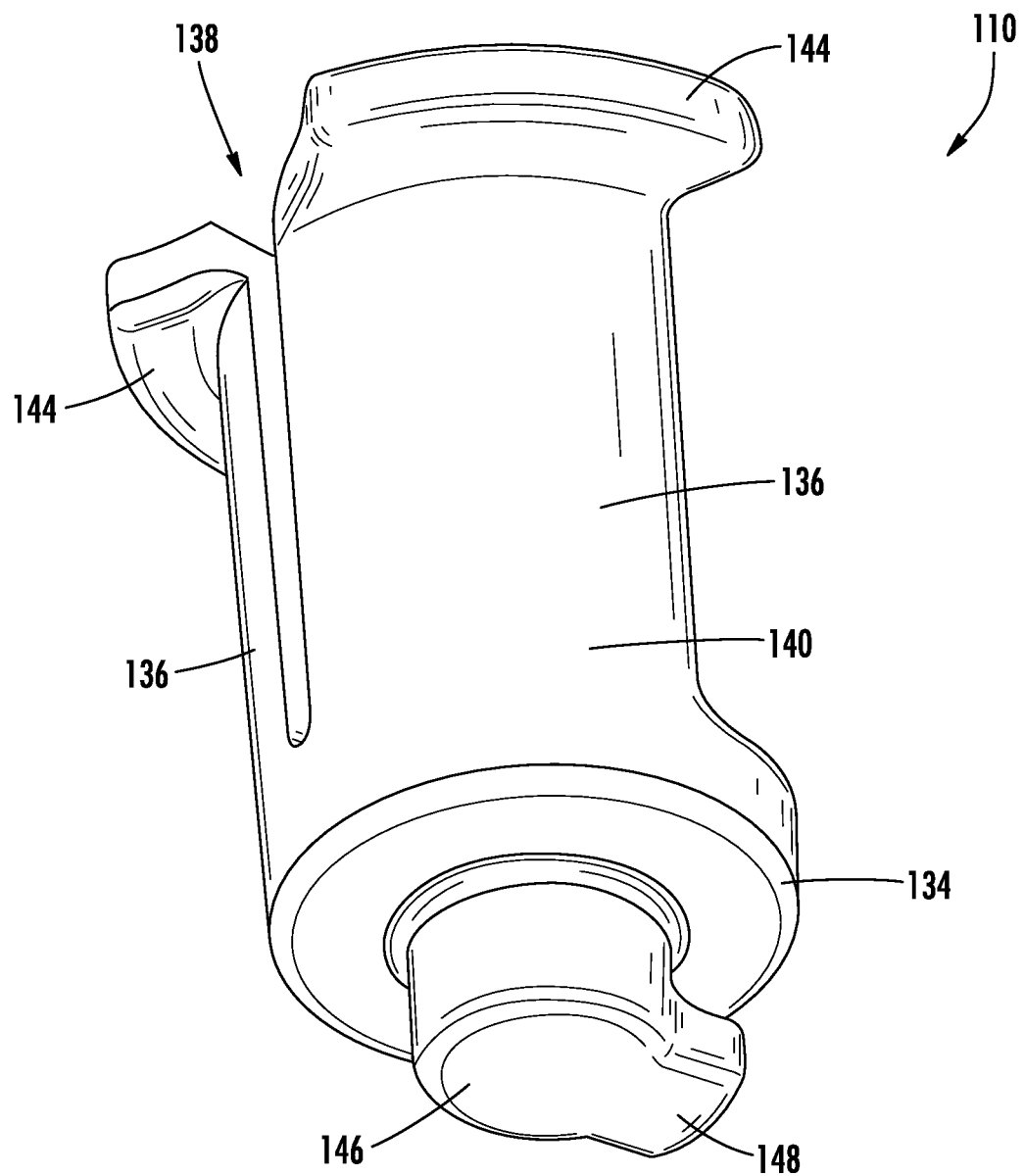
FIG. 9 is a bottom front perspective view of the swivel head of the circumferential dental matrix band retainer of FIG. 1.
Figure 10:
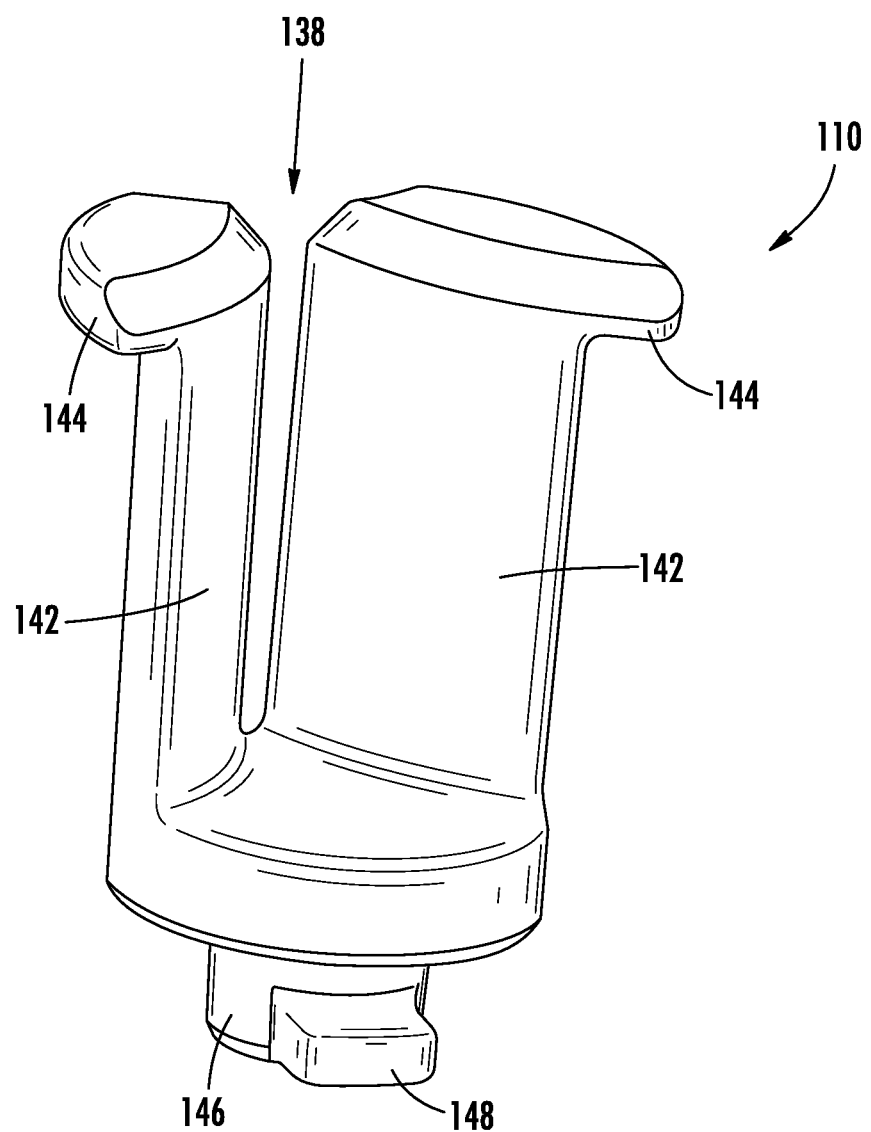
FIG. 10 is a top rear perspective view of the swivel head of the circumferential dental matrix band retainer of FIG. 1.

As seen in FIGS. 9 and 10, the swivel head includes a generally cylindrical base portion 134. A pair of walls 136 extends vertically from the base portion towards the top side of the retainer. The vertical walls are split by a vertical slot 138. The outer surfaces 140 of the vertical walls provide or define a generally cylindrical surface. The inner surfaces 142 of the vertical walls each define a convex surface which converge toward the slit. A ridge 144 extends laterally outward from a top edge of each of the vertical walls. A stub 146 having a diameter slightly smaller than the diameter of the circular opening extends downward from the base. A tang or extension 148 extends laterally from the stub and is spaced apart from the lower surface of the base a distance approximately the same as the thickness of the second bottom wall at the undercut. The stub and tang define a profile similar to the keyhole opening. It will be understood that the tang must be aligned with the slot in order for the swivel head to be installed in the main body portion. The swivel head is then rotated about 180 degrees past one of the stops. The swivel head may then be positioned with the vertical slot generally towards the proximal end of the retainer, with the swivel head in an interference fit but easily adjustable about a 225 degree position with the tang between the two stops.

It will be understood that the retractor is received within the channel and surrounded by the side walls, bottom walls and top wall. The coupler is adjacent the head portion, separated by the structure therebetween, with the two outer bows in the normally arched configuration. When the bows are squeezed toward one another, the distal end of the retractor is moved distally relative to the head portion, thus moving the coupler in a like distal direction away from the head portion.

The retainer is operated as follows. The closed end of a matrix band is placed into the retainer through the slot of the coupler with the movable buckle of the matrix band in front of the head portion and the stationery tail positioned within the coupler of the proximal end of the retractor. The loop portion of the matrix band is placed over the tooth. The tensioner bows are squeezed causing the retractor to retract and pulling the closed end of the band back, forcing the buckle forward towards the loop portion of the matrix band, forming a tight fit around the tooth. When the matrix band is in position, the tensioner can be removed and the free end of the band flattened so that it is out of the way.

In another embodiment, the head portion includes four vertical prongs (not shown) extending vertically upward from the second bottom side. The four prongs define four vertical slits, one facing distal, another facing proximal, another on one side of the channel and the other on the opposite side of the channel.

In another embodiment, the coupler of the retractor consists of two vertical flanges (not shown) forming a slit. The slit is aligned with the longitudinal axis of the channel.

The swivel head allows the band to be used on the left or right side of the head. Similarly, the four vertical posts provide the ability for the retainer to be used on either side of the jaw.

The main body portion and, in particular, the flexible arms are made of a material and formed in a manner in which the flexible arms are biased in the bow shaped position as shown in the drawings.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A dental matrix band retainer comprising:
    a retractor having a proximal end and a distal end, with a band engagement portion at the proximal end;
    a main body portion having a proximal end and a distal end, and a longitudinally extending portion at the proximal end of the main body portion, the longitudinally extending portion having a proximal and a distal end, and the main body portion includes a head portion located at the proximal end of the main body portion; and
    a spring bias mechanism coupling the retractor to the main body portion, the spring bias mechanism includes a pair of flexible bow shaped arms, the bow shaped arms having a proximal end and a distal end, the distal ends of the bow shaped arms are coupled at the distal end of the retractor, the proximal ends of the bow shaped arms are coupled to the distal end of the longitudinally extending portion, the spring biased mechanism having a static position and a fully active position, wherein in the static position the head portion is spaced apart from the band engagement portion a first distance, and in the fully active position the head portion is spaced apart from the band engagement portion a second distance which is greater than the first distance, the flexible bow shaped arms provide an actuator for urging the spring bias mechanism towards the fully active position.

2. The dental matrix band retainer of claim 1, wherein the main body portion includes the bow shaped arms.

3. The dental matrix band retainer of claim 1, wherein the longitudinally extending portion includes a channel, wherein at least a portion of the retractor extends within the channel, the main body portion further including a wall between the head portion and the channel, wherein a main body band receiving slot substantially divides the wall.

4. The dental matrix band retainer of claim 1, wherein the head portion includes a movable toggle abutment face, the face including a head portion band receiving slot.

5. The dental matrix band retainer of claim 4, wherein the head portion includes a generally cylindrical shaped receptacle; and
    a generally cylindrical shaped swivel head received by the generally cylindrical shaped receptacle.

6. The dental matrix band retainer of claim 5, wherein the generally Cylindrical shaped swivel head includes a disc shaped base, with two walls which extend upward from the base, the two walls are divided by the head portion band receiving slot, the two walls generally form a cylindrical outer surface, and each wall defines a convex internal surface, the convex internal surfaces diverging to form the head portion band receiving slot, each wall having an upper portion from which extend a ridge in a lateral direction, the generally cylindrical shaped receptacle includes an opening with an undercut and a slot, a cylindrical stub extends from the bottom of the swivel head to be received by the undercut opening, the cylindrical stub includes a tang extending laterally and is shaped to be received via the opening and slot in a generally rearward facing direction to allow subsequent locking engagement.

7. The dental matrix band retainer of claim 1, wherein the retractor and main body portion are a unitary component.

8. The dental matrix band retainer of claim 1, wherein the retractor includes a rod portion extending between the band engagement portion and the distal end, and the distal end includes a connector for attachment to a connector at the distal end of the main body portion, the band engagement portion includes a coupler having a stationary toggle receptacle, and a retractor band receiving slot extending from the receptacle towards and opening at the proximal end of the retractor, the retractor and the channel include a tongue and groove interface for stability.

9. A dental matrix band retainer comprising:
    a retractor having a proximal end and a distal end, with a band engagement portion at the proximal end;
    a main body portion having a proximal end and a distal end, with a head portion located at the proximal end, the head portion includes a generally cylindrical shaped receptacle;
    a generally cylindrical shaped swivel head received by the generally cylindrical shaped receptacle,
    the generally cylindrical shaped swivel head includes a disc shaped base with two walls which extend upward from the base, the two walls are divided by a face band receiving slot, the two walls generally form a cylindrical outer surface, and each of said two walls defines a convex internal surface, the convex internal surfaces diverging to form the face band receiving slot, each of said two walls having an upper portion from extend a ridge in a lateral direction;
    the generally cylindrical shaped receptacle includes an opening with an undercut and a slot, a cylindrical stub extends from a bottom of the swivel head to be received by the opening, the cylindrical stub includes a tang extending laterally and is shaped to be received via the opening and the slot in a generally rearward facing direction to allow subsequent locking engagement; and
    a bias mechanism coupling the retractor to the main body portion, the bias mechanism having a static position and a fully active position, the bias mechanism including a pair of flexible bow shaped arms, wherein in the static position the head portion is spaced apart from the band engagement portion a first distance, and in the fully active position the head portion is spaced apart from the band engagement portion a second distance which is greater than the first distance, the flexible bow shaped arms provide an actuator for urging the spring bias mechanism towards the fully active position.

* * * * *